(12) United States Patent
Oberbauer et al.

(10) Patent No.: US 8,338,096 B2
(45) Date of Patent: Dec. 25, 2012

(54) MARKERS OF ACUTE KIDNEY FAILURE

(75) Inventors: Rainer Oberbauer, Vienna (AT);
Alexander Kainz, Viena (AT); Bernd Mayer, Vienna (AT); Paul Perco, Vienna (AT)

(73) Assignee: Rainer Oberbauer, Vienna (AT)

( * ) Notice: Subject to any disclaimer, the term of this patent is extended or adjusted under 35 U.S.C. 154(b) by 0 days.

(21) Appl. No.: 12/937,716

(22) PCT Filed: Apr. 15, 2009

(86) PCT No.: PCT/EP2009/054439
§ 371 (c)(1),
(2), (4) Date: Nov. 23, 2010

(87) PCT Pub. No.: WO2009/127644
PCT Pub. Date: Oct. 22, 2009

(65) Prior Publication Data
US 2011/0059857 A1 Mar. 10, 2011

(30) Foreign Application Priority Data

Apr. 15, 2008 (EP) .................................... 08450055

(51) Int. Cl.
*C12Q 1/68* (2006.01)
*G01N 33/00* (2006.01)
(52) U.S. Cl. ...... 435/6.1; 435/6.12; 435/6.18; 435/6.19; 435/6.11; 435/7.92
(58) Field of Classification Search ........................ None
See application file for complete search history.

(56) References Cited

U.S. PATENT DOCUMENTS

2006/0008804 A1 * 1/2006 Chibout et al. ................... 435/6

OTHER PUBLICATIONS

Dubinski et al., Activated cells in urine and monocyte chemotactic peptide-1 (MCP-1)—Sensitive rejection markers in renal graft recipients; Transplant Immunology, vol. 18, pp. 203-207, 2008.*
Zhou et al., Expression of Neuropilin-1 in Kidney Graft Biopsies: What Is the Significance?; Transplantation Proceedings, vol. 39, pp. 81-83, 2007.*
Collins et al., The application of genomic and proteomic technologies in predictive, preventive and personalized medicine; Vascular Pharmacology, vol. 45, pp. 258-267, 2006.*
Kawashima et al., Identification and characterization of ligands for L-selectin in the kidney. I. Versican, a large chondroitin sulfate proteoglycan, is a ligand for L-selectin; International Immunology, vol. 11, No. 3, pp. 393-405, 1999.*
Kranz et al., Acute antibody-mediated rejection in paediatric renal transplant recipients; Pediatr Nephrol, vol. 26, pp. 1149-1156, 2011.*
Perco et al., Protein biomarkers associated with acute renal failure and chronic kidney disease; Eur J Clinical Investigation, vol. 36, pp. 753-763, 2006.*

* cited by examiner

*Primary Examiner* — Ardin Marschel
*Assistant Examiner* — Addison D Ault
(74) *Attorney, Agent, or Firm* — Michael Fedrick; Loza & Loza, LLP

(57) ABSTRACT

The present invention relates to the method of determining the risk of acute kidney injury comprising determining the amount of a marker selected from VCAN, NRP1, CCL2, CCL19, COL3A1, GZMM or any combination thereof in a sample.

16 Claims, 6 Drawing Sheets

MARKERS OF ACUTE KIDNEY FAILURE

CROSS-REFERENCE TO RELATED APPLICATIONS

Figure 1:
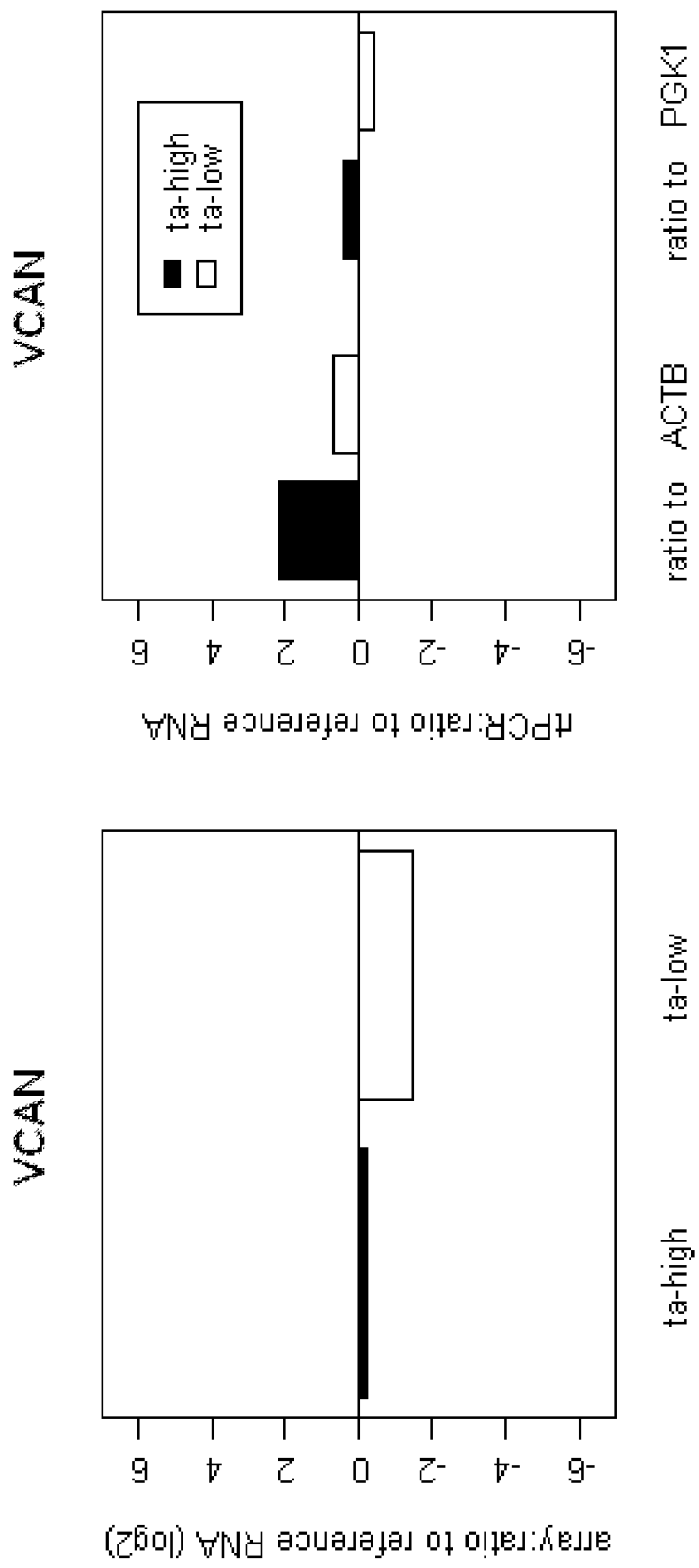

This application is the U.S. national stage of International Patent Application No. PCT/EP2009/054439, filed on Apr. 15, 2009 and entitled MARKERS OF ACUTE KIDNEY FAILURE, which claims the benefit of priority from European Patent Application No. O8450055.2, filed Apr. 15, 2008. The disclosures of the foregoing applications are incorporated herein by reference in their entirety.

The present invention relates to a method for detection, diagnosis, prognosis, or monitoring the risk of acute kidney injury (AKI) by measuring a panel of biomarkers. In particular, the invention refers to a predisposition testing.

AKI is in the clinical setting described as acute renal failure (ARF) or acute tubular necrosis (ATN) and refers to the spontaneous and significant decrease in renal function. AKI therefore reflects the entire spectrum of ARF, recognizing that an acute decline in kidney function is often secondary to an injury that causes functional or structural changes in the kidneys. ARF is a frequent and serious problem with a variety of adverse short- and long-term clinical consequences. Loss of function of the kidney, a vital organ, in the form of acute renal failure represents a special hazard, in particular to older patients, despite modern therapies including the use of the various forms of artificial kidney. In diagnosis and prognosis care must be taken to differentiate between functional renal insufficiency and intrinsic injury with morphologic damage.

AKI in particular in the intensive care unit is often associated with multiple organ failure and sepsis. Furthermore, AKI is associated with high mortality and morbidity in humans. Patients, for instance, experience AKI in ischemic reperfusion injury, along with treatment with nephrotoxic compounds including but not limited to antibiotics or anticancer drugs, application of contrast media e.g. when performing angiography resulting in nephropathy or nephrotoxicity, or at the intensive care unit, e.g. in the context of sepsis. The annual number of patients receiving contrast media is more than 100 million in the developed countries, and the rate of acute kidney injury ranges in a percent range, if coupled to risk factors like hypotension or diabetes.

AKI is usually categorised according to pre-renal, intrinsic and post-renal causes.

Pre-Renal (Causes in the Blood Supply):
hypovolemia (decreased blood volume), usually from shock or dehydration and fluid loss or excessive diuretics use.
hepatorenal syndrome, in which renal perfusion is compromised in liver failure
vascular problems, such as atheroembolic disease and renal vein thrombosis (which can occur as a complication of the nephrotic syndrome)
infection usually sepsis, systemic inflammation due to infection
severe burns
sequestration due to pericarditis and pancreatitis
hypotension due to antihypertensives and vasodilators
Intrinsic (Damage to the Kidney Itself):
toxins or medication (e.g. some NSAIDs, aminoglycoside antibiotics, iodinated contrast, lithium, phosphate nephropathy due to bowel preparation for colonoscopy with sodium phosphates)
rhabdomyolysis (breakdown of muscle tissue)—the resultant release of myoglobin in the blood affects the kidney; it can be caused by injury (especially crush injury and extensive blunt trauma), statins, stimulants and some other drugs
hemolysis (breakdown of red blood cells)—the hemoglobin damages the tubules; it may be caused by various conditions such as sickle-cell disease, and lupus erythematosus
multiple myeloma, either due to hypercalcemia or "cast nephropathy" (multiple myeloma can also cause chronic renal failure by a different mechanism)
acute glomerulonephritis which may be due to a variety of causes, such as anti glomerular basement membrane disease/Goodpasture's syndrome, Wegener's granulomatosis or acute lupus nephritis with systemic lupus erythematosus Post-Renal (Obstructive Causes in the Urinary Tract) Due to:
medication interfering with normal bladder emptying (e.g. anticholinergics).
benign prostatic hypertrophy or prostate cancer.
kidney stones.
due to abdominal malignancy (e.g. ovarian cancer, colorectal cancer).
obstructed urinary catheter.
drugs that can cause crystalluria and drugs that can lead to myoglobinuria and cystitis According to the state of the art, renal failure is diagnosed when either creatinine or blood urea nitrogen tests are markedly elevated in an ill patient, especially when oliguria is present. Previous measurements of renal function may offer comparison, which is especially important if a patient is known to have chronic renal failure as well. If the cause is not apparent, a large amount of blood tests and examination of a urine specimen is typically performed to elucidate the cause of acute renal failure, medical ultrasonography of the renal tract is essential to rule out obstruction of the urinary tract.

An exemplary consensus criterium for the diagnosis of AKI is at least one of the following:
Risk: serum creatinine increased 1.5 times or urine production of less than 0.5 ml/kg body weight for 6 hours
Injury: creatinine 2.0 times OR urine production less than 0.5 ml/kg for 12 h
Failure: creatinine 3.0 times OR creatinine more than 355 μmol/l (with a rise of more than 44) or urine output below 0.3 ml/kg for 24 h
Loss: persistent AKI or complete loss of kidney function for more than four weeks
End-stage Renal Disease: complete loss of kidney function for more than three months.

A rapid increase in serum creatinine may also be an indicator for a high AKI risk following medical treatment, e.g. an impairment in renal function is indicated by an increase in serum creatinine by more than 0.5 mg/dl or more than 25% within 3 days after medication.

Kidney biopsy may be performed in the setting of acute renal failure, to provide a definitive diagnosis and sometimes an idea of the prognosis, unless the cause is clear and appropriate screening investigations are reassuringly negative.

To diagnose AKI, usually urine and blood tests are done and the volume of urine produced is monitored.

The gold standard for diagnosing AKI is the measurement of serum creatinine. Unfortunately, creatinine as marker has several limitations. On the one hand, levels of serum creatinine widely vary among individuals depending on age, sex, muscle mass or medication status. On the other hand, serum creatinine does not accurately depict kidney function during acute changes in glomerular filtration as it is a marker, which can only be interpreted in steady state. Furthermore creatinine levels do not rise until damage is severe and kidney function already declines. Other biomarkers such as lipocalin 2 (LCN2), also known as NGAL (neutrophil gelatinase-associated lipocalin), kidney injury molecule 1 (KIM1), cysteine-rich angiogenic inducer 61 (CYR61), or interleukin 18 (IL18) have recently been proposed as alternative parameters for the detection of acute kidney injury.

WO2008/017306A1 describes a diagnostic test to exclude significant renal injury by measuring neutrophil gelatinase-associated lipocalin (NGAL).

WO2007/013919A2 describes human Gro-alpha as a marker of acute kidney injury.

Perco et al (European Journal of Clinical Investigation (2006) 36, 753-763) describe protein biomarkers associated with acute renal failure and chronic kidney disease.

WO2004/088276A2 discloses the detection of renal tubular cell injury and renal failure utilizing NGAL as a biomarker.

Hauser et al (Laboratory Investigation (2004) 84, 353-361) describe a gene-expression pattern of donor kidney biopsies. The differences in gene-expression between kidneys from living and cadaveric organ donors are determined. Among other genes, versican was upregulated in samples from cadaveric donors as compared to samples from living donors.

US2007/0249002A1 discloses systems and methods for characterizing kidney diseases by detection of cytokines, cytokine-related compounds and chemokines in urine, among them monocyte chemotactic protein-1 (MCP-1). Rice et al (Renal Failure (2002) 24(6), 703-723) disclose that monocyte chemoattractant protein-1 expression correlates with monocyte infiltration in the post-ischemic kidney. MCP-1 is reportedly increased by ischemia-reperfusion injury.

Grandaliano et al (Transplantation (1997) 63(3), 414-420) describe the MCP-1 expression and monocyte infiltration in acute renal transplant rejection.

Jee Ko et al (Nephrol Dial Transplant (2008) 23, 842-852) describe ischemia/reperfusion as a major cause of acute kidney injury and quantification of inflammatory markers, among them MCP-1.

Maier et al (Shock (2000) 14(2), 187-192) describe massive chemokine transcription, among them MCP-1, in acute renal failure due to polymicrobial sepsis.

Wang et al (J Am Soc Nephrol (2002) 13, 548A) describe the upregulated chemokine gene expression, such as MCP-1, in endotoxemic acute renal failure.

Moon et al (J Korean Med Sci (2007) 22, 810-4) associate polymorphisms in MCP-1 promoter with diabetic kidney failure.

WO2005/054502A2 discloses a method for diagnosing rejection in a transplanted subject. A list of biomarkers indicative for transplant rejection is provided.

Akalin et al (Transplantation (2001) 72, 948-953) perform a gene expression analysis in human renal allograft biopsy samples, and determine gene transcripts that are upregulated during acute rejection.

Langer et al (J Am Soc Nephrol (2004) 15, 2893-2901) describe CCL19 as a marker of allograft rejection.

Yang et al (Nephrol Dial Transplant (2007) 22, 445-456) describe the assessment of tubulointerstitial injury by immunohistochemical methods, which determine several antigens, such as collagen III.

Yoshida et al (Biochemical and Biophysical Research Communications (2002) 291, 787-794) describe the gene expression in renal ischemia-reperfusion. Among the genes upregulated in the AKI model was procollagen type III alpha 1 (Col3a1).

Forbes et al (Kidney International (2000) 57, 375-385) describe the histology of changes in ischemic acute renal failure. Interstitial collagen III was increased during the first few days, followed by a decrease.

Mishra et al (J Am Soc Nephrol (2003) 14, 2534-2543) describe Lipocalin as a urinary biomarker for ischemic renal injury.

WO2007/104537A2 describes methods for assessing acute transplant rejection.

Some of the gene expression products are also known to play a role in neovascularisation and inflammation:

WO2007/096142A2 describes vascular tumor markers, such as versican, and a method for identifying diseases associated with neovascularisation.

WO2005/010213A2 describes markers for detection of gastric cancer, such as chondroitin sulphate proteoglycan 2 (CSPG2).

WO2005/024603A2 describes a method for detecting, diagnosing and treating human renal cell carcinoma. Differential gene expressions in normal renal epithelial cells and renal cell carcinomas are identified. Among others, neuropilin 1 is determined to be differentially expressed.

Latil et al (Int. J. Cancer (Pred. Oncol.) (2000) 89, 167-171) disclose Neuropilin-1 overexpression in metastatic tumors.

Kreuter et al (Leukemia (2006) 20, 1950-1954) describe the correlation of neuropilin-1 overexpression to survival in acute myeloid leukemia.

WO99/55855A2 describes neuropilin antisense oligonucleotides sequences to inhibit the growth of tumor cells.

WO2007/056470A2 describes anti-NRP1 antibodies capable of inhibiting a neuropilin mediated biological activity.

WO2007/041623A2 describe methods for diagnosis in systemic inflammatory response syndromes employing several markers, among them CCL19.

Krumbholz et al (Journal of Neuroimmunology (2007) 190, 72-79) disclose the upregulation of CCL19 in neuroinflammation.

Pao et al (The Journal of Immunology (2005) 175, 3235-3245) describe the role of granzyme M in immunity to infection.

EP0913692A1 describes an immunoassay for procollagen-III-C-terminal propeptide, using specifically binding antibodies.

Chen et al (J Mol Cell Cardial (2000) 32, 1805-1819) describe connective tissue growth factor and TGF-beta mRNA levels that were increased following myocardial infarction, which correlated well with concomitant increases of other markers, among them type III collagen mRNA.

Krenacs et al (Blood (2003) 101(9), 3590-3593) describe the expression of serine protease granzyme M in lymphoma.

Bade et al (International Immunology (2005) 17(11) 1419-1428) describe the differential expression of granzymes A, K and M in human peripheral blood lymphocytes.

Sayers et al (The Journal of Immunology (2001) 166, 765-771) describe the restricted expression of granzyme M in human lymphocytes using specific antibodies.

Patients with normal kidney function are currently not tested for any renal disease biomarkers. In the absence of any functional kidney disorder, such as urine volume reduction or creatinine level, it is assumed that there is no risk for developing AKI. However, there are patients, who have the potential to develop AKI upon certain medical treatment, which could be damaging to the kidney function, such as simple radiography using a contrast medium or chemotherapy. Several risk factors for acute renal failure have been identified so far.

High-risk patients are considered those with chronic diseases that can affect the kidneys like diabetes, hypertension and heart disease. Pregnant patients who suffer from eclampsia, a hypertensive condition, also have a high risk for kidney damage.

Some drugs are nephrotoxic, i.e. poisonous to the kidney, and therefore damaging to the kidneys. This includes certain antibiotics like aminoglycosides, anti-inflammatory drugs and the contrast media used in specific X-ray tests of the urinary tract. A need therefore exists for a marker which can be used to specifically and reproducibly detect the presence of, or predisposition to acquiring AKI clinically leading to ARF.

It is the object of the present invention to provide markers to identify patients with early onset of AKI or predisposition for experiencing ARF.

According to the invention there is provided a method of determining the risk of acute kidney injury in a patient, by determining a kidney risk factor (KRF) in a sample from said patient, which KRF is selected from the group consisting of VCAN, NRP1, CCL2, CCL19, COL3A1 and GZMM. The risk of AKI also refers to the AKI predisposition and prognosis of developing AKI or ARF, respectively. Thus, it is understood that an individual at risk of AKI also has a predisposition and prognosis of developing AKI and/or ARF. In particular, the risk of genuine AKI is determined according to the invention. It is understood that the diagnostic method according to the invention commonly is employing ex vivo, in particular in vitro testing.

Preferably the method according to the invention comprises determining the level of said KRF, which is at least 1.2 times increased, preferably at least 1.5 times increased, compared to a control.

In a method according to the invention, which employs the determination of at least two of said KRF, the preferred level of each KRF is at least 1.2 times increased compared to a control, to distinguish patients at risk of AKI.

In a preferred embodiment the expression of KRF is determined in said sample, such as the polypeptide or polynucleotide level of said KRF.

The preferred method according to the invention employs a sample, which is selected from the group consisting of tissue or physiological fluids, such as blood, serum, plasma or urine sample. Less preferred, but possible, is the determination of a KRF in an invasive sample, such as a biopsy sample. Further preferred samples are obtained from tissues, extracts, cell cultures, cell lysates and lavage fluid.

The condition, which can be detected with the inventive methods is in particular a patient at risk of developing AKI, which can e.g. be determined by using a kidney biopsy sample and also by detecting the markers in serum, blood, plasma or urine by comparing reference values of non-progressive renal disease values or from healthy subjects.

Preferably the method according to the invention is applied to a patient, who is suffering from a chronic disease, such as metabolic disease, diabetes, hypertension or heart disease.

In another preferred embodiment the patient is tested for the risk status according to the invention before receiving potentially nephrotoxic medication.

According to a preferred method, the KRF is determined by microarray hybridization with specific probes or by PCR.

In another aspect, the invention refers to a panel of biomarkers for determining acute renal failure or the AKI risk, consisting of at least two markers selected from the group consisting of VCAN, NRP1, CCL2, CCL19, COL3A1 and GZMM. It is therefore contemplated that one or more of said biomarkers are used to manufacture a diagnostic product to determine AKI or the AKI risk.

Thus, a set of reagents for determining the AKI risk is preferably specifically binding to at least two markers of the panel according to the invention.

The preferred set according to the invention comprises reagents, which are ligands specifically binding to said markers.

Preferably the ligands are nucleotide sequence specific oligonucleotides or antibodies or antibody fragments. It is further preferred that the reagents are labelled.

Therefore, the present invention provides a method of detection, diagnosis, prognosis, monitoring or predisposition testing of acute kidney injury by determining the amount of a marker selected from VCAN, NRP1, CCL2, CCL19, COL3A1, GZMM or any combination thereof in a sample. For the inventive method, one of these markers can be detected, or a combination of any two, three, four, five, or six of these markers, or any combination with at least one of the markers according to the invention with a further risk factor associated with AKI.

The inventive markers are:

1. VCAN—Versican (UniGene: Hs.643801, Hs.715773, GeneID: 1462, GenBank: AA056022/AA056070): Versican is a major extracellular chondroitin sulfate proteoglycan detected in the vessel wall, where it contributes to the formation of blood vessels. It is highly expressed by aortic endothelial cells and vascular smooth muscle cells.

2. NRP1—Neuropilin 1 (UniGene: Hs.131704, GeneID: 8829, GenBank: AA098867/AA099262): NRP1 is a membrane-bound coreceptor to a tyrosine kinase receptor for both vascular endothelial growth factor (VEGF; MIM 192240) and semaphorin (see SEMA3A; MIM 603961) family members. NRP1 plays versatile roles in angiogenesis, axon guidance, cell survival, migration, and invasion.

3. CCL2—chemokine (C—C motif) ligand 2 (UniGene: Hs.303649, GeneID: 6347, GenBank: T77817/T77816): This gene is one of several cytokine genes clustered on the q-arm of chromosome 17. Cytokines are a family of secreted proteins involved in immunoregulatory and inflammatory processes. The protein encoded by this gene is structurally related to the CXC subfamily of cytokines. Members of this subfamily are characterized by two cysteines separated by a single amino acid. This cytokine displays chemotactic activity for monocytes and basophils but not for neutrophils or eosinophils. It has been implicated in the pathogenesis of diseases characterized by monocytic infiltrates, like psoriasis, rheumatoid arthritis and atherosclerosis. It binds to chemokine receptors CCR2 and CCR4.

4. CCL19—chemokine (C—C motif) ligand 19 (UniGene: Hs.50002, GeneID: 6363, GenBank: AA680186): This gene is one of several CC cytokine genes clustered on the p-arm of chromosome 9. Cytokines are a family of secreted proteins involved in immunoregulatory and inflammatory processes. The CC cytokines are proteins characterized by two adjacent cysteines. The cytokine encoded by this gene may play a role in normal lymphocyte recirculation and homing. It also plays an important role in trafficking of T cells in thymus, and in T cell and B cell migration to secondary lymphoid organs. It specifically binds to chemokine receptor CCR7.

5. COL3A1—collagen, type III, alpha 1 (UniGene: Hs.443625, GeneID: 1281, GenBank: A1679372): This gene encodes the pro-alpha1 chains of type III collagen, a fibrillar collagen that is found in extensible connective tissues such as skin, lung, uterus, intestine and the vascular system, frequently in association with type I collagen. Mutations in this gene are associated with Ehlers-Danlos syndrome types IV, and with aortic and arterial aneurysms. Two transcripts, resulting from the use of alternate polyadenylation signals, have been identified for this gene.

6. GZMM—granzyme M (lymphocyte met-ase 1) (UniGene: Hs.465511, GeneID: 3004, GenBank: AI124941): Human natural killer (NK) cells and activated lymphocytes express and store a distinct subset of neutral serine proteases together with proteoglycans and other immune effector molecules in large cytoplasmic granules. These serine proteases are collectively termed granzymes and include 4 distinct gene products: granzyme A, granzyme B, granzyme H, and Met-ase, also known as granzyme M.

These markers, including but not limited to respective polypeptides and nucleotide sequences, such as native-sequence polypeptides, isoforms, chimeric polypeptides, any derivative, part or polymorphism (including without limitation splice variant) of such biomolecules, all homologs, fragments, and precursors of the markers, and modified forms of the polypeptides and derivatives, or nucleic acids encoding such polypeptides, are referred to herein as "Kidney Risk Factors (s)" (KRF).

Thus, the present invention provides a panel of biomarkers that can be used in a method for detection, diagnosis, prognosis, or monitoring the acute kidney injury (AKI), including the risk for experiencing acute renal failure (ARF) In particular, the inventive method allows the determination of the predisposition for developing AKI or respective risk stages, e.g. to distinguish between low, medium and high risk patients.

In a specific embodiment, the invention contemplates marker sets containing or consisting essentially of at least two, three, four, five or six KRF, wherein at least one of the KRFs is selected from the inventive panel, preferably at least two, three, four, five or six of the KRFs according to the invention. The marker sets are preferably polypeptide or genetic marker sets representing the KRF or respective binders, e.g. comprising a plurality of respective polypeptides, genes or polynucleotides.

KRF are thus preferably determined by testing for KRF polypeptides and KRF polynucleotides. In the following, KRF determination always refers to the detection and/or testing for one or more KRF polypeptides or KRF polynucleotides. KRF determination is specifically proposed in the method according to the invention for determining the risk for developing an acute kidney disease or an acute kidney disorder, and in particular in the detection of the risk of developing AKI within a short, medium or long-term period, depending on medical treatment and care. Besides determining the predisposition or risk status of a patient, the markers can be used for diagnosis, monitoring, i.e. monitoring progression or therapeutic treatment, prognosis, treatment, or classification of respective kidney disease, or as markers before or after therapy.

Preferably those patients are tested for KRF with normal kidney function, where no kidney disease is diagnosed. Normal kidney function is defined as a glomerular filtration rate above 70 ml/min, preferably above 80 ml/min, more preferably above 90 ml/min and essentially no proteinuria. Other endocrine functions are of no relevance in this proposal and thus not discussed here.

The identification of a patient's risk or predisposition is essential in the patient population that is already classified as high-risk patients. It is thus preferred to test a patient population according to the invention, which is already classified as risk patients, for instance, patients with risk factors of age, preexisting chronic illness, malnutrition, cancer, severe trauma, or sepsis. In particular, it is indicated to test patients suffering from metabolic disease, such as diabetic disease, hypertension or heart or vascular disease, Typically, patients suffering from AKI are not tested for the AKI risk according to the invention.

The inventive method can also include the step of obtaining the sample from a patient at risk for developing acute kidney injury, e.g. before contrast medium administration in the course of angiography. Thus, the term "patients" herein always includes healthy subjects. The subject can, e.g., be any mammal, in particular a human, but also selected from mouse, rat, hamster, cat, dog, horse, cow, pig, etc.

Reference values for the KRF are preferably obtained from a control group of patients or subjects with normal expression of said KRF, or a KRF expression, that is afflicted with kidney stress conditions, such as septic, cancer or diabetic patients, without proteinuremia or AKI, which represents the appropriate reference patient group. In a particular aspect, the control comprises material derived from a pool of samples from normal patients.

Thus, the method according to the invention is specifically provided for determining susceptibility to kidney disease, such as AKI, by determining a KRF in a patient comprising:
(a) obtaining a sample from a patient,
(b) detecting or identifying in the sample a KRF, and
(c) comparing the detected amount with an amount detected for a reference.

The term "detect" or "detecting" includes assaying, imaging or otherwise establishing the presence or absence of the target KRF encoding the markers, subunits thereof, or combinations of reagent bound targets, and the like, or assaying for, imaging, ascertaining, establishing, or otherwise determining one or more factual characteristics of kidney disease or similar conditions. The term encompasses diagnostic, prognostic, and monitoring applications for a KRF.

The invention also provides a method of assessing whether a patient is at risk of AKI, comprising comparing:
(a) levels of a KRF in a sample from said patient, and
(b) normal levels of a KRF in samples of the same type obtained from control patients, wherein altered levels of the KRF relative to the corresponding normal levels is an indication that the patient has an AKI risk, e.g. a predisposition to kidney disease, such as AKI, in particular where detection of a level of KRF that differs significantly from the standard indicates acute kidney disease or onset of kidney disease or increased risk for developing ARF. A significant difference between the levels of a KRF in a patient and the normal levels is an indication that the patient has a risk of kidney disease or a predisposition to kidney disease, such as AKI.

In a preferred embodiment, the method according to the invention for assessing whether a patient has a risk of kidney disease or a pre-disposition for kidney disease, higher levels of KRF in a sample relative to the corresponding normal levels is an indication that the patient has kidney disease or a pre-disposition for kidney disease.

The risk of acute kidney injury is indicated if the amount of a marker or the combination of markers is increased at least 1.2 times the reference value of subjects not suffering from AKI, preferably being subjects from a control group or healthy subjects. Usually an increase below a 1.5 fold increase of an individual marker reflects a relatively low risk; at least 1.5 fold, but below 2.0 fold increase is considered a medium risk; at least 2.0 fold increase would indicate a high-risk. If at least two KRFs are increased, the risk is considered to be increased as well. Thus, at least 1.2-1.4 fold increase of each of at least two KRFs already determines the medium to high-risk stages.

In special embodiments the amount of VCAN is at least 1.5, preferably at least 1.6, at least 1.8, at least 2, at least 3, or at least 4 times the reference value, in particular as determined by PCR with ACTB (actin beta) as endogenous control or as determined by microarray analysis.

In special embodiments the amount of NRP1 is at least 1.5, preferably at least 1.6, at least 1.8, at least 2, at least 3, or at least 4 times the reference value, in particular as determined by PCR with ACTB as endogenous control or as determined by microarray analysis.

In special embodiments the amount of CCL2 is at least 1.2, preferably at least 1.5, more preferably at least 1.6, at least 1.8, at least 2, at least 3 or at least 4 times the reference value, in particular as determined by PCR with ACTB as endogenous control or as determined by microarray analysis.

In special embodiments the amount of CCL19 is at least 1.5, preferably at least 1.6, at least 1.8, at least 2, at least 3, or at least 4 times the reference value, in particular as determined by PCR with ACTB as endogenous control or as determined by microarray analysis.

In special embodiments the amount of COL3A1 is at least 1.2, preferably at least 1.5, more preferably at least 1.6, at least 1.8, at least 2, at least 3 or at least 4 times the reference value, in particular as determined by PCR with ACTB as endogenous control or as determined by microarray analysis.

In special embodiments the amount of GZMM is at least 1.5, preferably at least 1.6, at least 1.8, at least 2, at least 3, or at least 4 times the reference value, in particular as determined by PCR with ACTB as endogenous control or as determined by microarray analysis.

If more than one marker is detected, the comparison is made to each single reference value for each marker in the reference itself. The inventive prognosis method can predict whether a patient is at risk of developing acute kidney injury. The higher the fold increase, the higher is the patient's risk of AKI. An elevated KRF indicates, for example, special treatment of the patient, using appropriate medication or contrast media. The method of the invention can thus be used to evaluate a patient before, during, and after medical treatment.

Likewise, the KRF level can be compared to a cut-off concentration and the kidney disease development potential is determined from the comparison; wherein concentrations of KRF above the reference concentrations are predictive of, e.g., correlate with, kidney disease development in the patient.

Thus, the preferred method according to the invention comprises the step of comparing the KRF level with a predetermined standard or cut-off value, which is preferably at least 50% higher than the standard, more preferred at least 60% or 70% higher, but can also be at least 100% higher.

In aspects of the methods of the invention, the methods are non-invasive for AKI predisposition testing, which in turn allow for diagnosis of a variety of conditions or diseases associated with acute kidney disease. In particular, the invention provides a non-invasive non-surgical method for detection, diagnosis, monitoring, or prediction of acute kidney disease or onset of kidney disease in a patient comprising: obtaining a sample of blood, plasma, serum, urine or saliva or a tissue sample from the patient; subjecting the sample to a procedure to detect one or more KRF by comparing the levels of KRF to the levels of KRF obtained from a control.

The invention also contemplates a method of assessing the potential of a test compound to contribute to kidney disease or onset of kidney disease comprising:

(a) maintaining separate aliquots of a sample from a patient in the presence and absence of the test compound, and (b) comparing the levels of one or more of KRF in each of the aliquots.

This is particularly useful in monitoring the KRF level in clinical trials. A significant difference between the levels of a KRF in an aliquot maintained in the presence of or exposed to the test compound relative to the aliquot maintained in the absence of the test compound, indicates that the test compound potentially contributes to kidney disease or onset of kidney disease.

Likewise, the invention according to the invention can be employed to determine the effect of an environmental factor on kidney disease comprising comparing one or more KRF associated with kidney disease or onset of kidney disease in the presence and absence of the environmental factor.

The inventive markers can be detected in any sample of a subject comprising said markers e.g. where an expression of a KRF is determined either as polynucleotide, e.g. as mRNA, or expressed polypeptide or protein. The comparison with the reference value should be of the same sample type.

In preferred embodiments, determining the amount of the marker or any combination thereof comprises determining the expression of the marker(s), preferably by determining the mRNA concentration of the marker(s). To this extent, mRNA of the sample can be isolated, if necessary, after adequate sample preparation steps, e.g. tissue homogenisation, and hybridized with marker specific probes, in particular on a microarray platform with or without amplification, or primers for PCR-based detection methods, e.g. PCR extension labelling with probes specific for a portion of the marker mRNA. In preferred embodiments the marker(s) or a combination thereof is (are) determined by microarray hybridization with VCAN, NRP1, CCL2, CCL19, COL3A1, GZMM specific probes or by PCR.

Differential expression of the polynucleotides is preferably determined by micro-array, hybridization or by amplification of the extracted polynucleotides. The invention contemplates a gene expression profile comprising one or more of the KRF that is associated with AKI predisposition. This profile provides a highly sensitive and specific test with both high positive and negative predictive values permitting diagnosis and prediction of the patient's risk of developing disease.

For example, the invention provides a method for determining the AKI risk in a patient comprising (a) contacting a sample obtained from said patient with oligonucleotides that hybridize to a KRF, and (b) detecting in the sample a level of polynucleotides that hybridize to the KRF relative to a predetermined cut-off value, and therefrom determining the AKI risk in the subject.

Within certain preferred embodiments, the amount of polynucleotides that are mRNA are detected via polymerase chain reaction using, for example, oligonucleotide primers that hybridize to a KRF, or complements of such polynucleotides. Within other embodiments, the amount of mRNA is detected using a hybridization technique, employing oligonucleotide probes that hybridize to a KRF, or complements thereof.

When using mRNA detection, the method may be carried out by combining isolated mRNA with reagents to convert to cDNA according to standard methods and analyzing the products to detect the presence of KRF in the sample.

In particular aspects of the invention, the methods described herein utilize one or more KRF placed on a microarray so that the expression status of each of the markers is assessed simultaneously. In an embodiment, the invention provides a microarray comprising a defined set of KRF genes, whose expression is significantly altered by an AKI risk. The invention further relates to the use of the microarray as a prognostic tool to predict kidney disease.

In further embodiments the amount of a marker or any combination thereof is determined by the polypeptide or protein concentration of the marker(s), e.g. with marker specific ligands, such as antibodies or specific binding partners. The binding event can, e.g., be detected by competitive or non-competitive methods, including the use of labelled ligand or marker specific moieties, e.g. antibodies, or labelled competitive moieties, including a labelled marker standard, which compete with marker proteins for the binding event. If the marker specific ligand is capable of forming a complex with the marker, the complex formation indicates expression of the markers in the sample.

In particular, the invention relates to a method for diagnosing and monitoring acute kidney disease in a patient by quantitating a KRF in a biological sample from the subject comprising
(a) reacting the biological sample with one or more binding agents specific for the KRF, e.g. an antibody that is directly or indirectly labelled with a detectable substance, and
(b) detecting the detectable substance.

KRF levels can be determined by constructing an antibody microarray, in which binding sites comprise immobilized, preferably monoclonal antibodies specific to a marker. The invention also relates to kits for carrying out the methods of the invention.

The invention further contemplates the methods, compositions, and kits described herein using additional markers associated with kidney disease. The methods described herein may be modified by including reagents to detect the additional markers, or polynucleotides for the markers.

Appropriate probes, specific antibodies or methods for determining the biomarkers are known in the art, and have been used for different purposes. For instance, mRNA and protein concentration of versican can be tested with respective diagnostic tools according to WO2007/096142A2 and WO2005/010213A2. NRP1 mRNA or protein concentration can be tested according to WO2005/024603A2. NRP1 specific oligonucleotides and NRP1 specific antibodies are described in WO99/55855A2 and WO2007/056470A2, respectively. CCL2 (MCP-1) specific antibodies are described in US2007/249002A1. Rice et al (2002, see above) describe the determination of MCP-1 mRNA or protein using the respective tools. WO2005/054503A2 discloses means to determine CCL19 mRNA or protein. Antibodies or oligonucleotides specific to COL3A1 have been described in EP0913692A1 and Chen et al (2000, see above), respectively. GZMM protein and nucleotide sequence can be determined using specific antibodies and PCR primers according to the teaching of Bade et al (2005, see above) and Sayers et al (2001, see above).

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dinitrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In exemplary embodiments, the analyte is measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards.

In a further aspect the present invention provides a set of at least two different marker specific moieties, each specific for a KRF to determine at least two KRFs, wherein at least one of the KRFs is selected from the panel according to the invention, e.g. more than two, three, four, five or six marker specific moieties, wherein at least two or more, such as three, four, five or six markers selected from VCAN, NRP1, CCL2, CCL19 COL3A1 or GZMM can be determined.

Preferred marker combinations can be derived from the examples and Table 4 below, which are reaching area under the curve (AUC) values of at least 0.8, preferably at least 0.85, more preferred at least 0.9, e.g. exemplarily VCAN, CCL2, and COL3A1 as well as VCAN and NRP1. Likewise, any combination of at least one KRF of the panel according to the invention with another KRF, which brings about an AUC value as described above, is considered a preferred combination to determine the AKI risk.

Marker specific moieties are substances which can bind to or detect at least one of the markers for a detection method described above and are in particular marker nucleotide sequence detecting tools or marker protein specific antibodies, including antibody fragments, such as Fab, F(ab), F(ab)', Fv, scFv, or single chain antibodies. The marker specific moieties can also be selected from marker nucleotide sequence specific oligonucleotides, which specifically bind to a portion of the marker sequences, e.g. mRNA or cDNA, or are complementary to such a portion in the sense or complementary anti-sense, like cDNA complementary strand, orientation.

For easy detection the moieties are preferably labelled, such as by optical, including fluorescence, and radioactive labels.

The present invention is further illustrated by the following figures and examples without being limited thereto.

FIGURES

Figure 2:
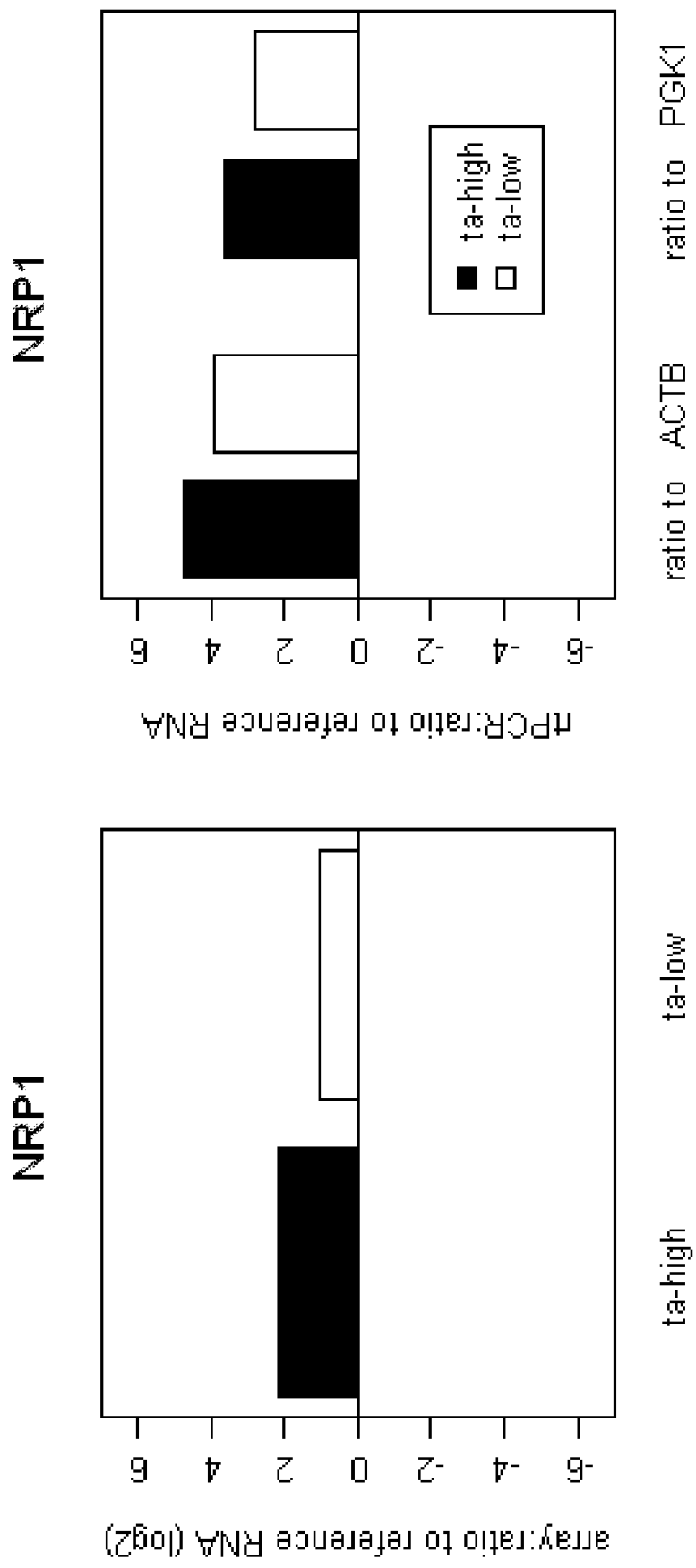
Figure 3:
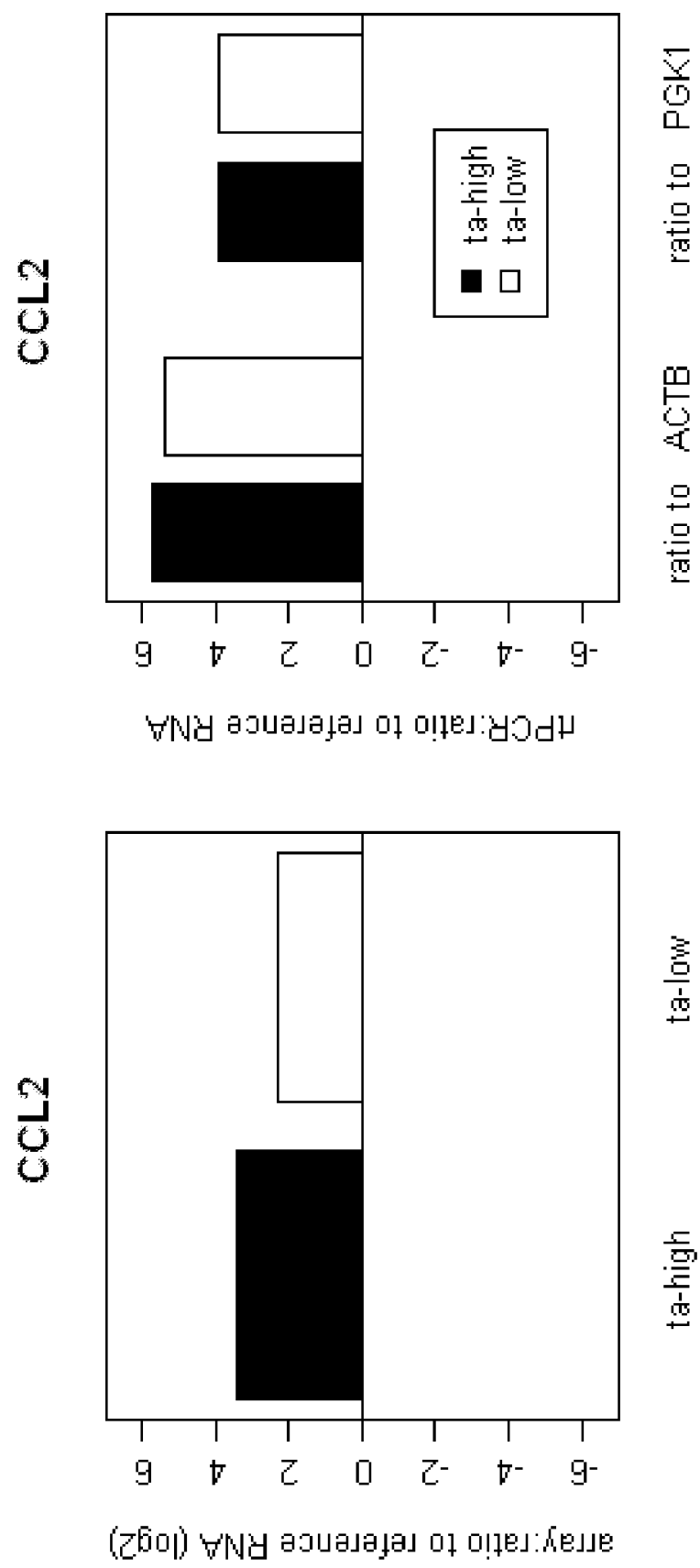
Figure 4:
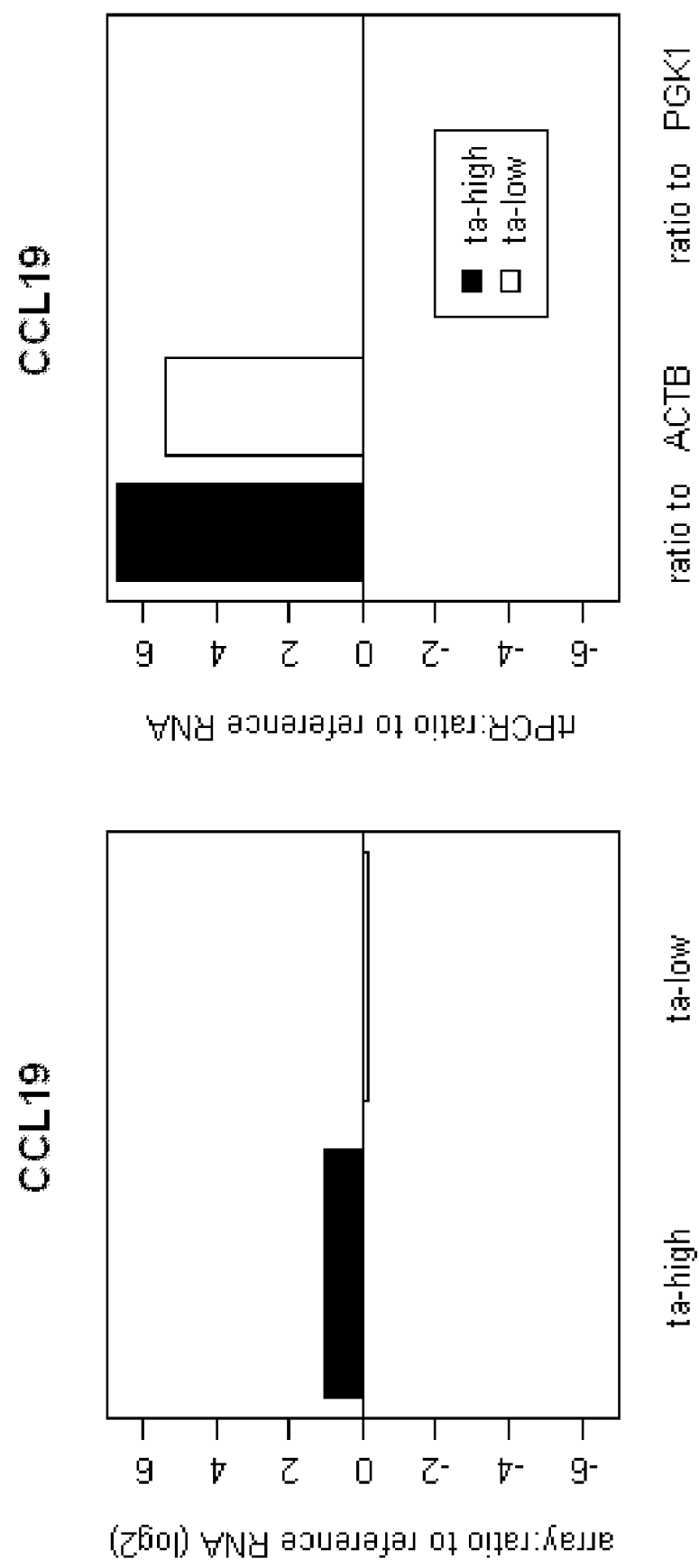
Figure 5:
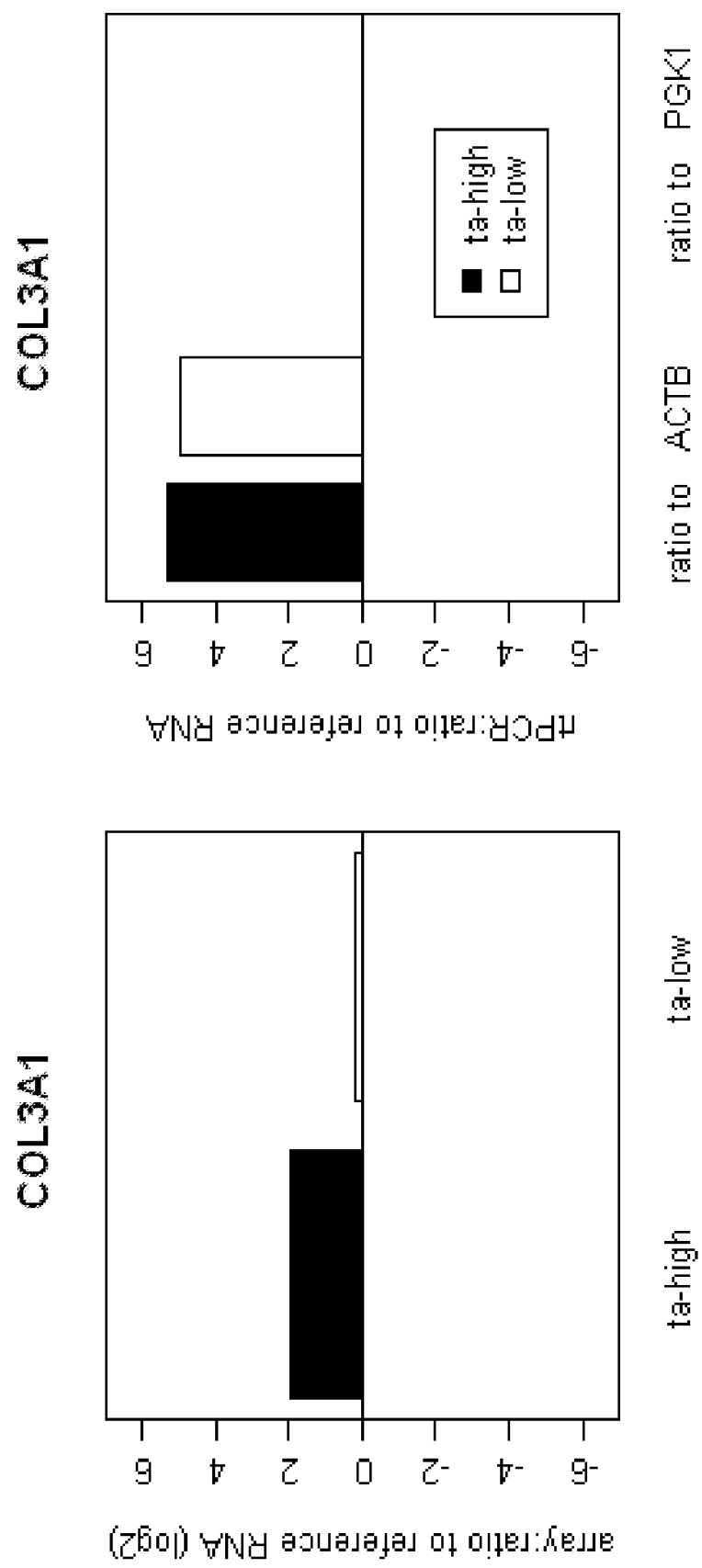
Figure 6:
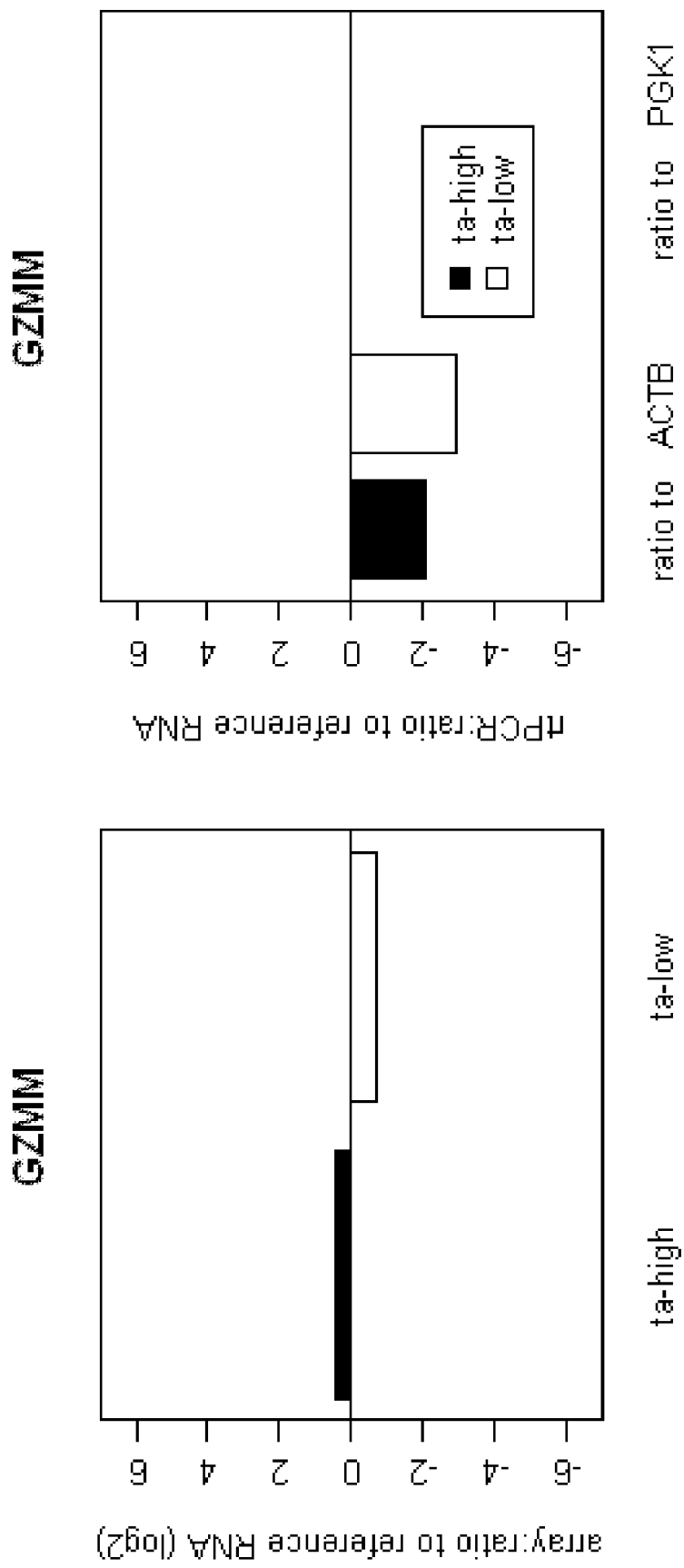

FIG. 1: Results for VCAN: Arrays: 11 ta-high vs 21 ta-low (fold-change for AA056022/AA056070: 2.40)
FIG. 2: Results for NRP1: Arrays: 11 ta-high vs 21 ta-low (fold-change for AA098867/AA099262: 2.16)
FIG. 3: Results for CCL2: Arrays: 11 ta-high vs 21 ta-low (fold-change for T77817/T77816: 2.19)
FIG. 4: Results for CCL19: Arrays: 11 ta-high vs 21 ta-low (fold-change for AA680186: 3.23)
FIG. 5: Results for COL3A1: Arrays: 11 ta-high vs 21 ta-low (fold-change for A1679372: 2.20)
FIG. 6: Results for GZMM: Arrays: 11 ta-high vs 21 ta-low (fold-change for AI124941: 2.18)

EXAMPLES

Example 1

Patient Samples

Human renal biopsies of kidney transplant donors were collected. 82 kidney biopsies were included for cDNA microarray analysis. Donor kidney biopsies were examined pre-transplantation by a pathologist and the degree of glomerulosclerosis (gs), arteriolosclerosis (as), interstitial fibrosis (if), interstitial inflammation (ii), tubular atrophy (tc) as well as acute tubulus damage (ta) was assessed following a semi-quantitative grading system: 0—no; 1—minor; 2—moderate; 3—severe damage. Based on the histological parameter of acute tubulus damage (ta) two groups were defined, namely those samples showing no or only minor tubulus damage (n=21) and the other group of samples with severe tubulus damage (n=11). Acute tubular damage is a histological parameter strongly correlated to acute kidney injury and thus was used to identify marker candidates separating samples with no or only mild damage versus samples with severe tubulus damage. Microarray-based gene expression profiling was performed in those 32 patients' samples, while real-time PCR validation experiments were performed in 18 samples.

Example 2

RNA Isolation and Microarray Hybridization

Sample preparation followed established experimental steps as described previously (Hauser et al. Lab Invest 2004, Kainz et al. Am J Transpl 2004). All organs were perfused with a histidine-tryptophan-ketoglutarat (HTK) cold preservation solution at 4° C. during organ procurement. Wedge biopsy of each kidney was performed under sterile conditions at the end of the cold ischemic time right before transplantation. The biopsy specimens were immediately submerged in RNAlater™ (Ambion, Austin, Tex.) and stored at 4° C. for not longer than five days.

Total RNA was isolated and purified using chloroform and trizol reagent (Invitrogen, Carlsbad, Calif.), and the RNA yield and quality was checked with the Agilent 2100 Bioanalyzer and RNA6000 LabChip® kit (Agilent, Palo Alto, Calif.). Stratagene Universal human reference RNA was used as reference (Stratagene, La Jolla, Calif.).

Two micrograms of isolated total RNA were amplified using the RiboAmp RNA amplification kit (Arcturus, Mountain View, Calif.). The amplified RNA was inspected on an ethidium bromide stained 1% agarose gel and on the Agilent 2100 Bioanalyzer.

cDNA microarrays holding 41,409 features were obtained from the Stanford University Functional Genomics core facility (batches No.: shcm, shdb, shem, sheo, sher, and shfr). A type II experimental setup was used, where each of the samples was hybridized along with a common reference to a microarray. Stratagene Universal human reference RNA, composed of total RNA from 10 human cell lines, served as reference. One microgram of sample and standard Stratagene Universal human reference RNA were labeled with CyScribe cDNA post labeling kit (Amersham Pharmacia Biotech, Buckinghamshire, UK) in a two-step procedure. Samples were loaded onto arrays and incubated for 16 hr in a water bath at 65° C. After three washing steps, the fluorescence images of the hybridized microarrays were examined using a GenePix 4100A scanner (Axon Instruments, Union City, Calif.). The GenePix Pro 4.1 software was used to grid images and to calculate spot intensities. The arrays were numbered according to the anonymous organ donor ID and were processed in random order.

Example 3

Statistical Analysis and Selection of Putative Biomarkers

Signals showing intensity signal over background values lower than 1.5 in either channel were excluded and the analyses were focused on genes with valid data in at least 80% of processed samples, leaving 24123 cDNA clones in the analysis dataset. A two-sample t-test ($p<0.05$) and the two-fold-change criterion were used to identify differentially expressed genes (DEGs) when comparing samples with no or only mild tubular damage versus samples with severe tubular damage.

The subcellular location of DEGs was determined using data stored in the SwissProt database as well as bioinformatics prediction routines based on the protein sequence, and secreted proteins were identified. The secreted DEGs showing the highest fold-change values were selected for validation via real-time PCR experiments.

Example 4

Validation Via Real-Time PCR

Real-time PCR was performed using the TaqMan Universal PCR Master Mix, TaqMan Gene expression assays (primers and TaqMan FAM-MGB with NFQ probes) with the ABI PRISM 7300 Sequence Detection System. The following Gene expression assays were used for the six markers CCL2, CCL19, VCAN, COL3A1, GZMM, NRP1 respectively: Hs00234140_m1, Hs00171149_m1, Hs00171642_m1, Hs00164103_m1, Hs00193417_m1, Hs00826128_m1. All instruments and reagents were purchased from Applied Biosystems. Relative gene expression values were evaluated with the 2-ΔΔCt method using ACTB (actin beta) as housekeeping gene and Stratagene Universal human reference RNA (Stratagene, La Jolla, Calif.) as reference RNA. This reference RNA was also used as the Standard RNA in the microarray experiments. qRT-PCR conditions according to the manufacture's (ABI) recommendations: 10 min 95° C., 40 cycles (15 sec 95° C., 1 min 60° C.) with fluorescence reading during annealing step.

Example 5

Microarray Analysis 22 differentially expressed transcripts mapping to 18 unique genes upregulated in the samples with severe acute tubular damage could be identified that had protein isoforms which were secreted according to information stored in the SwissProt database. We selected 10 of the 18 genes for quantitative real-time PCR verification experiments. Selection of these 10 was based on fold-changes, p-values, as well as information on gene function as derived from scientific literature. These genes are versican (VCAN), neuropilin 1 (NRP1), chemokine (C—C motif) ligand 2 (CCL2), chemokine (C—C motif) ligand 19 (CCL19), collagen type III alpha 1 (COL3A1), granzyme M (GZMM), apolipoprotein B (APOB), complement factor H(CFH), ficolin 1 (FCN1), and fibrinogen-like 2 (FGL2).

TABLE 1

Results

| GeneName | GeneSymbol | p-value | Fold-change (array) |
|---|---|---|---|
| Versican | VCAN | 0.0005 | 2.40 |
| Neuropilin 1 | NRP1 | 0.0109 | 2.16 |
| chemokine (C-C motif) ligand 2 | CCL2 | 0.0141 | 2.19 |
| chemokine (C-C motif) ligand 19 | CCL19 | 0.0275 | 3.23 |
| collagen, type III, alpha 1 | COL3A1 | 0.0175 | 2.20 |
| granzyme M | GZMM | 0.0150 | 2.18 |
| apolipoprotein B | APOB | 0.0457 | 3.59 |
| complement factor H | CFH | 0.0118 | 2.15 |
| ficolin 1 | FCN1 | 0.0041 | 2.43 |
| fibrinogen-like 2 | FGL2 | 0.0313 | 2.00 |

Example 6

Validation Via Real-Time PCR

The upregulation of six biomarkers could be validated in rtPCR experiments, namely VCAN, NRP1, CCL2, CCL19, COL3A1, and GZMM.

TABLE 2

Results

| GeneName | Gene-Symbol | p-value | Fold-change (array) | Fold-change (rtPCR to ACTB) |
|---|---|---|---|---|
| Versican | VCAN | 0.0005 | 2.40 | 2.85 |
| Neuropilin 1 | NRP1 | 0.0109 | 2.16 | 1.8 |
| chemokine (C-C motif) ligand 2 | CCL2 | 0.0141 | 2.19 | 1.26 |
| chemokine (C-C motif) ligand 19 | CCL19 | 0.0275 | 3.23 | 2.55 |
| collagen, type III, alpha 1 | COL3A1 | 0.0175 | 2.20 | 1.28 |
| granzyme M | GZMM | 0.0150 | 2.18 | 1.86 |
| apolipoprotein B | APOB | 0.0457 | 3.59 | -1.36 |
| complement factor H | CFH | 0.0118 | 2.15 | -1.75 |
| ficolin 1 | FCN1 | 0.0041 | 2.43 | -1.07 |
| fibrinogen-like 2 | FGL2 | 0.0313 | 2.00 | -2.06 |

Example 7 rtPCR Results in Proximal and Distal Tubule Cells

Renal cell suspensions were prepared from unaffected parts of tumor nephrectomies. Informed consent was obtained from all patients included in the study. Cortical tissue (approximately 0.5 cm$^3$) was dissected by removing the inner medulla and the outer fibrous capsule followed by mechanical homogenization using a clean scalpel. Minced sample were then pressed through a cell dissociation sieve (SIGMA ALDRICH) and transferred into medium M199 (Invitrogen, Carlsbad, Calif.) supplemented with 10% foetal calf serum (Invitrogen, Carlsbad, Calif.), using the plunger of a larger syringe. The obtained suspension was then further passed through a 40 μm cell strainer (BD-Biosciences) in order to obtain a nearly homogenous single cell suspension of renal tubular cells. Single cell suspension was then labelled with a PE-conjugated CD13 antibody (BD-Biosciences, San Jose, Calif.) and a FITC-conjugated Tamm Horse Fall antibody (Cedarlanes) specific for proximal or distal tubules, respectively. Cells were washed twice with MACS-buffer (Miltenyi-Biotec) and subjected to fluorescence activated cell sorting on a FACSAria cell sorter (BD-Biosciences). Typically, proximal and distal tubule cells ranged between 1-5% in the initial cell suspension. Cell yields after cell sorting were about 500.000 cells at purities of >95% for both proximal and distal tubule cells. Total RNA was isolated and purified using trizol (Invitrogen, Carlsbad, Calif.) and chloroform (Chornczynski P et al. Anal Biochem 1987 162:156-9).

Expression profiles of the six KRFs (CCL2, CCL19, VCAN, COL3A1, GZMM, NRP1) as well as two highly expressed genes in proximal and distal tubule cells, SLC34A1 and UMOD respectively, were analyzed by real time PCR. Total RNA was used for cDNA synthesis with the High Capacity cDNA Reverse Transcription Kit (Part No. 4368814). Real time PCR was performed using TaqMan Gene Expression Master Mix (Part No. 4369016) and TaqMan Gene expression assays (CCL2-Hs00234140_m1, CCL19-Hs00171149_m1, VCAN-Hs00171642_m1, COL3A1-Hs00164103_m1, GZMM-Hs00193417_m1, NRP1-Hs00826128_m1, SLC34A1-Hs00161828_m1, UMOD-Hs00358451_m1) on an ABI 7300 Sequence Detection System. Relative gene expression values were evaluated with the 2-ΔΔCt method using ACTB (Hs99999903_m1, beta actin) as housekeeping genes and Stratagene Universal human reference RNA (Stratagene, La Jolla, Calif.) as reference. All instruments and real time PCR reagents were purchased by Applied Biosystems (Foster City, Calif., USA). The log 2 relative expression values of sample to Stratagene Universal human reference RNA are depicted in the table below. The expression of all KRFs in distal tubule cells was higher as compared to Stratagene Universal human reference RNA. CCL19, COL3A1, and NRP1 also showed higher expression levels in proximal tubule cells as compared to Stratagene Universal human reference RNA.

TABLE 3

The log2 relative expression values of sample to standard reference RNA of the six KDFs along with two highly abundant proteins in tubuli tissue are given.

| KDFs | Expression in distal tubule cells | Expression in proximal tubule cells |
| --- | --- | --- |
| CCL2 | 2.93 | −0.16 |
| CCL19 | 10.93 | 3.56 |
| VCAN | 1.28 | −2.22 |
| COL3A1 | 1.75 | 0.43 |
| GZMM | 1.23 | −3.28 |
| NRP1 | 1.86 | 2.02 |
| SLC34A1 | 10.18 | 14.42 |
| UMOD | 14.61 | 8.21 |

Example 8 p-Values for Specific Combinations

Based on gene expression data of the six KRFs under study we established prediction rules in order to discriminate between the binary outcome acute tubular damage or no acute tubular damage. We assessed the ability of the prediction rule by calculating the area under the ROC curve (AUC) using the Somer's D statistic. The relation between the area under the ROC and Somer's D is AUC=(1+Somer's D)/2. AUC values of 1.0 indicate complete discrimination of the two groups based on the marker values, whereas values of 0.5 indicate random assignment.

In this study the best single predictor of progression with an AUC value of 0.886 is VCAN, followed by COL3A1 (AUC=0.804) and GZMM (AUC=0.794). Preferred marker combinations reaching AUC values greater than 0.9 are exemplarily VCAN, CCL2, and COL3A1, as well as VCAN and NRP1. A complete listing of AUC values of the respective markers and marker combinations based on gene expression data is given in the table below.

TABLE 4

Results

| Number | Model | AUC |
| --- | --- | --- |
| 1 | VCAN | 0.886 |
| 2 | CCL2 | 0.777 |
| 3 | COL3A1 | 0.804 |
| 4 | GZMM | 0.794 |
| 5 | CCL19 | 0.759 |
| 6 | NRP1 | 0.777 |
| 7 | VCAN CCL2 | 0.892 |
| 8 | VCAN COL3A1 | 0.922 |
| 9 | VCAN GZMM | 0.843 |
| 10 | VCAN CCL19 | 0.902 |
| 11 | VCAN NRP1 | 1.000 |
| 12 | CCL2 COL3A1 | 0.916 |
| 13 | CCL2 GZMM | 0.833 |
| 14 | CCL2 CCL19 | 0.879 |
| 15 | CCL2 NRP1 | 0.866 |
| 16 | COL3A1 GZMM | 0.931 |
| 17 | COL3A1 CCL19 | 0.819 |
| 18 | COL3A1 NRP1 | 0.822 |
| 19 | GZMM CCL19 | 0.847 |
| 20 | GZMM NRP1 | 0.800 |
| 21 | CCL19 NRP1 | 0.796 |
| 22 | VCAN CCL2 COL3A1 | 0.940 |
| 23 | VCAN CCL2 GZMM | 0.872 |
| 24 | VCAN CCL2 CCL19 | 0.909 |
| 25 | VCAN CCL2 NRP1 | 1.000 |
| 26 | VCAN COL3A1 GZMM | 0.941 |
| 27 | VCAN COL3A1 CCL19 | 0.924 |
| 28 | VCAN COL3A1 NRP1 | 1.000 |
| 29 | VCAN GZMM CCL19 | 0.894 |
| 30 | VCAN GZMM NRP1 | 1.000 |
| 31 | VCAN CCL19 NRP1 | 1.000 |
| 32 | CCL2 COL3A1 GZMM | 0.901 |
| 33 | CCL2 COL3A1 CCL19 | 0.924 |
| 34 | CCL2 COL3A1 NRP1 | 0.900 |
| 35 | CCL2 GZMM CCL19 | 0.835 |
| 36 | CCL2 GZMM NRP1 | 0.800 |
| 37 | CCL2 CCL19 NRP1 | 0.906 |
| 38 | COL3A1 GZMM CCL19 | 0.941 |
| 39 | COL3A1 GZMM NRP1 | 0.816 |
| 40 | COL3A1 CCL19 NRP1 | 0.843 |
| 41 | GZMM CCL19 NRP1 | 0.933 |
| 42 | VCAN CCL2 COL3A1 GZMM | 0.921 |
| 43 | VCAN CCL2 COL3A1 CCL19 | 0.939 |
| 44 | VCAN CCL2 COL3A1 NRP1 | 1.000 |
| 45 | VCAN CCL2 GZMM CCL19 | 0.905 |
| 46 | VCAN CCL2 GZMM NRP1 | 1.000 |
| 47 | VCAN CCL2 CCL19 NRP1 | 1.000 |
| 48 | VCAN COL3A1 GZMM CCL19 | 0.952 |
| 49 | VCAN COL3A1 GZMM NRP1 | 1.000 |
| 50 | VCAN COL3A1 CCL19 NRP1 | 1.000 |
| 51 | VCAN GZMM CCL19 NRP1 | 1.000 |
| 52 | CCL2 COL3A1 GZMM CCL19 | 0.941 |
| 53 | CCL2 COL3A1 GZMM NRP1 | 0.850 |
| 54 | CCL2 COL3A1 CCL19 NRP1 | 0.937 |
| 55 | CCL2 GZMM CCL19 NRP1 | 0.933 |
| 56 | COL3A1 GZMM CCL19 NRP1 | 1.000 |
| 57 | VCAN CCL2 COL3A1 GZMM CCL19 | 0.952 |
| 58 | VCAN CCL2 COL3A1 GZMM NRP1 | 1.000 |
| 59 | VCAN CCL2 COL3A1 CCL19 NRP1 | 1.000 |
| 60 | VCAN CCL2 GZMM CCL19 NRP1 | 1.000 |
| 61 | VCAN COL3A1 GZMM CCL19 NRP1 | 1.000 |

TABLE 4-continued

Results

| Number | Model | AUC |
|---|---|---|
| 62 | CCL2 COL3A1 GZMM CCL19 NRP1 | 1.000 |
| 63 | VCAN CCL2 COL3A1 GZMM CCL19 | 1.000 |

Example 9

Clinical Correlation

Nephrotoxic substances like antibiotics, anti-inflammatory drugs or contrast media used in specific X-ray tests may lead to acute kidney injury. One of these substances is iodinated contrast medium in coronary angiography. A sera sample collection of patients undergoing coronary angiography was initiated. One sample was collected before coronary angiography and second sample was collected 24 hours after coronary angiography. Creatinine values were determined as well as the estimated glomerular filtration rate according to the formula developed at the Mayo Clinic in Rochester (Ann Intern Med. 2004; 141: 929-937). According to the European Society of Urogenital Radiology, contrast-induced AKI is defined as impairment in renal function indicated by an increase in serum creatinine by >0.5 mg/dl or >25% within 3 days after contrast medium administration. Determination of KRF(s) in serum samples taken before contrast medium administration allow determining the correlation to the change in serum creatinine levels thus evaluating the potential to predict AKI.

The concentration of KRF(s) protein in serum samples is measured via ELISA technology using means well-known in the art. In brief, for a sandwich ELISA setup one monoclonal antibody directed against a specific KRF is adsorbed to wells of a 96 well polystyrene microplate, followed by incubation with human serum test samples and standards at various dilutions. After a washing step to get rid of unbound substances a second biotinylated detection antibody is added to each well followed by addition of HRP (horseradish peroxidase)-labeled streptavidin. Finally, ABTS (2,2'-Azino-bis-(3-ethylbenziazoline-6-sulfonic acid)) is introduced and the absorption is recorded. The absorption intensity is proportional to the amount of KRF in the sample. Data are evaluated by comparison to a standard, thus resulting in quantitative concentration values for the specific KRF in human serum samples under investigation.

The invention claimed is:

1. A method of determining the risk for acute kidney injury disease in a patient comprising the steps of:
measuring a concentration of at least one kidney risk factor (KRF) in a sample from said patient;
comparing the measured KRF concentration to a control value; and
determining the patient's risk of acute kidney injury based on comparing the measured KRF concentration to the control value,
wherein the at least one KRF is a predictor of disease progression and is CCL19.

2. A method of determining the risk for acute kidney injury disease in a patient comprising the steps of:
measuring a concentration of at least one kidney risk factor (KRF) in a sample from said patient;
comparing the measured KRF concentration to a control value; and
determining the patient's risk of acute kidney injury based on comparing the measured KRF concentration to the control value,
wherein the at least one KRF is a predictor of disease progression and is GZMM.

3. The method according to claim 1, wherein the level of said KRF is at least 1.2 times increased compared to a control.

4. The method according to claim 1, further comprising a step of calculating an area under a receiver operating characteristic (ROC) curve, wherein the area under the ROC curve associated with the KRF is at least 0.8 using the Somer's D statistic.

5. The method according to claim 1, wherein the expression of KRF is determined in said sample.

6. The method according to claim 1, wherein a polypeptide or polynucleotide level of said KRF is determined.

7. The method according to claim 1, wherein said sample is selected from the group consisting of tissue, blood, serum, plasma and a urine sample.

8. The method according to claim 1, wherein said patient is tested before receiving nephrotoxic medication.

9. The method according to claim 1, wherein said KRF is determined by microarray hybridization with specific probes or by PCR.

10. The method according to claim 2, wherein the level of said KRF is at least 1.2 times increased compared to a control.

11. The method according to claim 2, further comprising a step of calculating an area under a receiver operating characteristic (ROC) curve, wherein the area under the ROC curve associated with the KRF is at least 0.8 using the Somer's D statistic.

12. The method according to claim 2, wherein the expression of KRF is determined in said sample.

13. The method according to claim 2, wherein a polypeptide or polynucleotide level of said KRF is determined.

14. The method according to claim 2, wherein said sample is selected from the group consisting of tissue, blood, serum, plasma and a urine sample.

15. The method according to claim 2, wherein said patient is tested before receiving nephrotoxic medication.

16. The method according to claim 2, wherein said KRF is determined by microarray hybridization with specific probes or by PCR.

* * * * *